(12) United States Patent
Petrick et al.

(10) Patent No.: US 6,404,852 B1
(45) Date of Patent: Jun. 11, 2002

(54) OVERHEAD REDUCTION DUE TO SCRUBBING OR PARTIAL READOUT OF X-RAY DETECTORS

(75) Inventors: Scott W. Petrick, Sussex; Christine Quong, Waukesha, both of WI (US)

(73) Assignee: GE Medical Systems Global Technology Company, Waukesha, WI (US)

( * ) Notice: Subject to any disclaimer, the term of this patent is extended or adjusted under 35 U.S.C. 154(b) by 0 days.

(21) Appl. No.: 09/681,300

(22) Filed: Mar. 15, 2001

(51) Int. Cl.$^7$ ................................................. H05G 1/64
(52) U.S. Cl. .................... 378/98.8; 250/370.09
(58) Field of Search ...................... 378/98.8; 250/370.09

(56) References Cited

U.S. PATENT DOCUMENTS 4,996,413 A    2/1991  McDaniels et al.
6,292,534 B1 *  9/2001  Linders et al. ............. 378/98.8

* cited by examiner

Primary Examiner—Craig E. Church
(74) Attorney, Agent, or Firm—McAndrews, Held & Malloy, Ltd.; Peter J. Vogel, Esq.; Michael A. Dellapenna, Esq.

(57) ABSTRACT

An x-ray system (14) reads data from a detector array (22) including detector elements (40) arranged in rows (R1–R280) and columns (C1–C1365). A first group of rows include unneeded data (R1–R127) while a second group of rows include data of interest (R128–R1152). Activation of the detector elements in relation to the exposure of a patient to x-rays to improve efficiency with which the data of interest is read is disclosed. An exposure control (34) activates an x-ray tube (15) to expose the detector to x-rays during a first time period (E1). The first group of rows (R1–R127) are activated at least partially before or during the first time period. The second group of rows (R128–R1152) are activated after the first time period. Data is read from the second group of rows after the first time period.

18 Claims, 4 Drawing Sheets

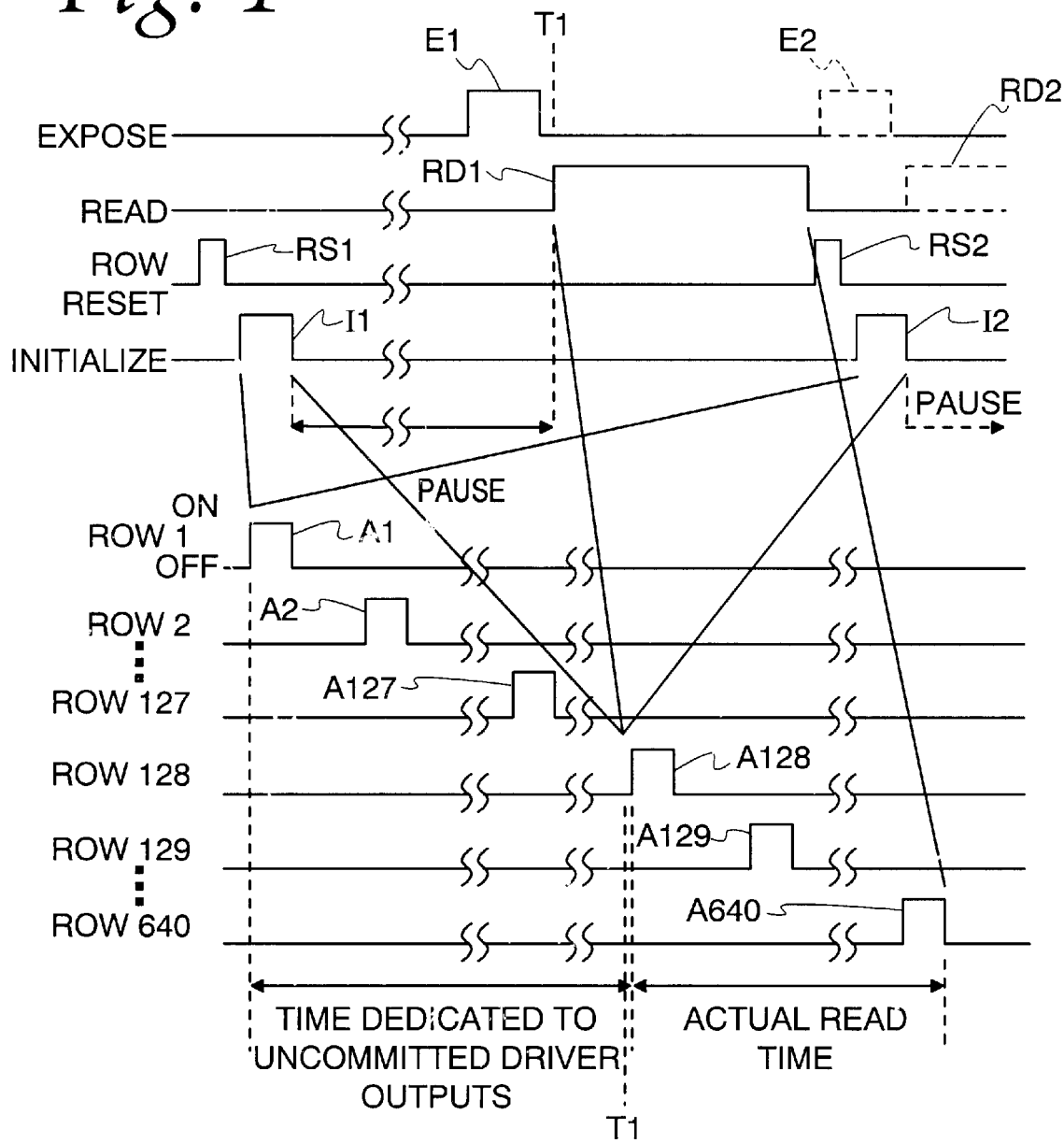

OVERHEAD REDUCTION DUE TO SCRUBBING OR PARTIAL READOUT OF X-RAY DETECTORS

BACKGROUND OF INVENTION

This invention relates to x-ray systems employing a solid state detector and more particularly relates to such systems in which data of interest occupies less than all elements of the detector.

Experience has shown that a modular design approach to x-ray detector control helps reduce the time to market. By using this approach, a common set of modular electronics may support three different detectors, such as a 41 cm square Radiographic detector, a 20 cm square Cardiographic detector, both consisting of square 0.2 mm pixels; and a Mammographic detector that is 23 cm×19.2 cm, consisting of square 0.1 mm pixels. The support electronics, consisting of drive modules to control the detector's field effect transistor (FET) switches and sense modules to read and convert the signal, may be 256 channel subsystems, designed to support detectors with 0.2 mm pixel pitch. Both the Cardiographic and Radiographic detectors may require an exact integer number of modules. The Mammographic detector, however, is different in a number of respects. It is rectangular and the pixel pitch is 0.1 mm. The smaller pitch is accommodated by sensing alternate channels from opposite sides, reducing the effective pitch of the sense electronics from 0.2 mm to 0.1 mm. The drive modules are similarly attached, although from two sets of (alternating) contacts that are on the same side in order to allow patient access to one edge of the detector. At first glance it would appear that both a non-integer number of drive and sense modules would be required. However, an exact multiple of 256 sense channels is required across the 19.2 cm dimension. The drive modules however would support 2560 channels, while only 2304 are required. An even number of modules may be required due to the manner in which the pitch mismatch between the detector and the module is managed, even though the requirements suggest that the problem could be solved with 9 (rather than 10) drive modules. This means that 128 drive channels are not committed to the detector on each end.

Given that the drive module consists of a custom Application Specific Integrated Circuit (ASIC), designed to function like a serial shift register with high voltage outputs, at least the first 128 uncommitted driver channels will require consideration during read out of the detector. The last 128 channels can be ignored due to the operation of module reset, which allows asynchronous reset of the shift register. One current FFDM x-ray detector is operated as if it consisted of 2432 scan lines. That is, the first 128 uncommitted drive channels are operated just like the following 2304 drive channels that are attached to detector scan lines, with the exception that the corresponding "image" data is not transferred out of the detector. This is because this data does not contain any X-Ray exposure information. However, operating the drive electronics in this manner imposes more than 5% of useless overhead (time).

Similarly, when smaller fields of view than the actual size of the detector are required, the scan lines not in the field of view will require scrubbing (that is the detector is read to restore the charge for each pixel, but the data is discarded). If the FETs are not scrubbed or read for long periods of time, the threshold voltage shifts (in an irreversible fashion) and the FETs no longer provide the necessary isolation when they are off, or conversely, may not provide low enough impedance when on to allow the pixel charge to be quickly and thoroughly restored, resulting in erroneous signal conversion in either case. If the scan lines outside the field of view are scrubbed in a fashion similar to the uncommitted drive channels of the FFDM detector, no advantage in read out time will be enjoyed by defining a smaller field of view on a larger detector. In order to support higher acquisition rates, a smaller detector would need to be substituted, which is a disadvantage in comparison to present Image Intensifier based systems which can easily switch between different field sizes. Conversely, a very complex readout algorithm shared between the detector and the X-Ray system could be defined which would be prone to error, corrupting the image acquisition in the process.

U.S. Pat. No. 4,996,413 discloses a split image x-ray detector that is read from the middle to the outside. Although this reading technique was an improvement in the art, subsequent research has shown that it is desirable for at least some applications to read the detector from the outside toward the middle. The present invention provides a technique for reading detectors that is an improvement on the teaching of U.S. Pat. No. 4,996,413.

The present invention addresses the foregoing problems and provides a solution.

SUMMARY OF INVENTION

The preferred embodiment is useful in an x-ray system for reading data from a detector array comprising detector elements arranged in rows and columns. The rows typically comprise a first plurality of rows including unneeded data and a second plurality of rows including data of interest. In such an environment, apparatus for coordinating the activation of the detector elements in relation to the exposure of a patient to x-rays to improve the efficiency with which the data of interest is read preferably comprises an x-ray tube generating x-rays. An exposure control is arranged to activate the x-ray tube to expose the detector to x-rays during a predetermined first time period. A detector controller is arranged to activate the first plurality of rows at least partially before or during the first time period and to activate the second plurality of rows after the first time period. An image processor is arranged to read the data in the second plurality of rows after the first time period.

Another embodiment includes a method analogous to the above-described apparatus.

By using the foregoing techniques, the overhead associated with scrubbing or partial read out of solid-state x-ray detectors can be substantially reduced.

BRIEF DESCRIPTION OF DRAWINGS

FIG. 4 is a timing diagram illustrating a preferred mode of operation of the apparatus show in FIG. 1.

DETAILED DESCRIPTION

In some present x-ray systems, read out of any of the detectors is initiated by the X-Ray system and is accomplished by releasing driver reset, initializing the drive ASIC, and alternating between enabling (the output of the shift register storing a "1") and clocking (the shift register to advance the stored "1" to the next bit). Uncommitted driver outputs are not operated any differently than driver outputs attached to detector scan lines. The operation of the uncommitted driver outputs take time that has no benefit and may impede faster acquisition rates that different applications may demand. A similar statement could be made about scan lines outside the field of view.

By using the preferred embodiment of the present invention, a different readout sequence is adopted by the detector. Specifically, the operation of uncommitted drive outputs or scan lines outside the field of view can be accomplished during the exposure time, masking the time required to do so in a manner that is transparent to the rest of the system.

Figure 1:
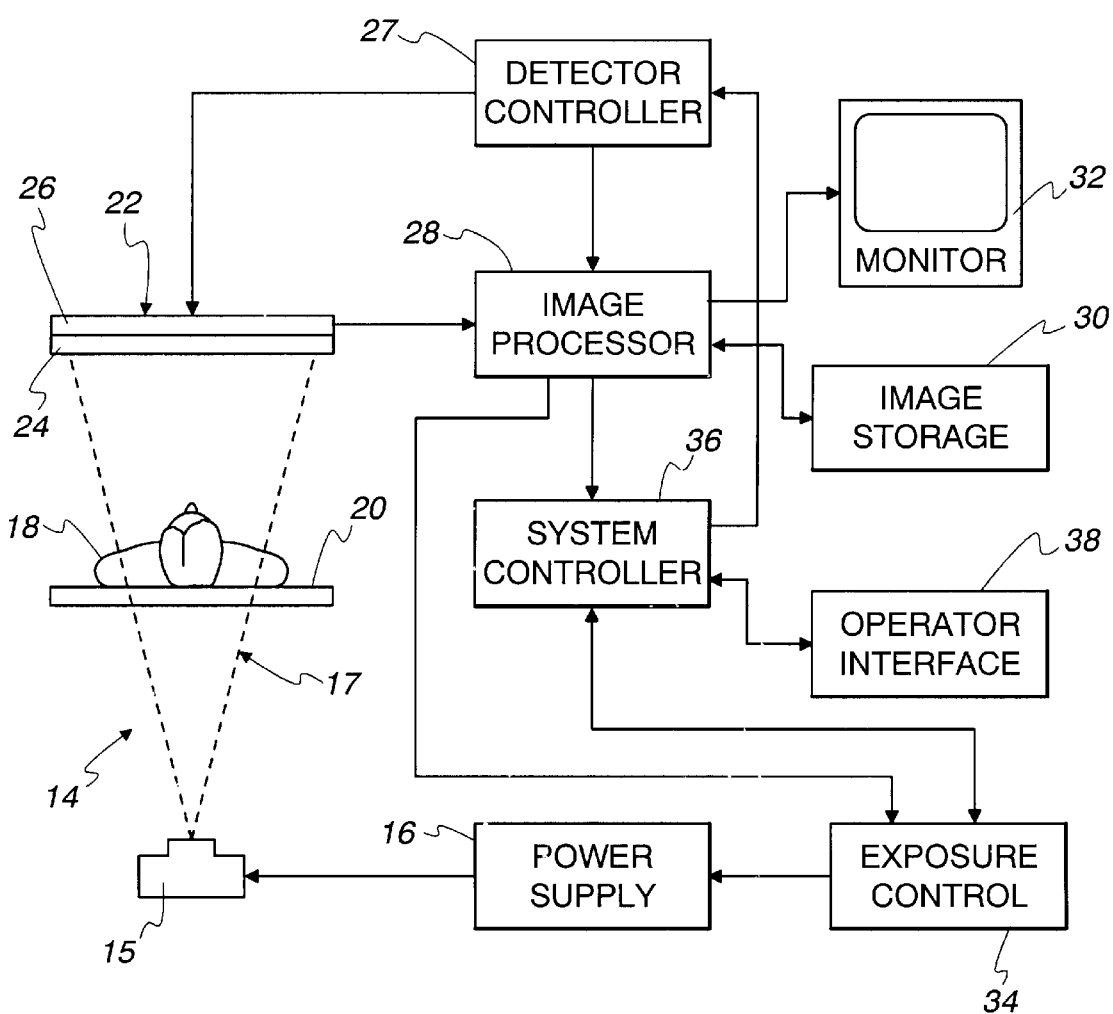
FIG. 1 is a schematic block diagram of a preferred form of x-ray system embodying the present invention and employing a solid-state detector.

Referring to FIG. 1, an X-ray system 14 made in accordance with the preferred embodiment includes an X ray tube 15 which, when excited by a power supply 16, emits an X-ray beam 17. As illustrated, the X-ray beam is directed toward a patient 18 lying on an X-ray transmissive table 20. The portion of the beam which is transmitted through the table and the patient impinges upon an X-ray detector designated 22. The X-ray detector 22 comprises a scintillator 24 that converts the X-ray photons to lower energy photons in the visible spectrum. Contiguous with the scintillator 24 is a photo detector array 26, which converts the light photons into an electrical signal. A detector controller 27 contains electronics for operating the detector array to acquire an image and to read out the signal from each photo detector element.

The output signal from the photo detector array 26 is coupled to an image processor 28 that includes circuitry for processing and enhancing the X ray image signal. The processed image then is displayed on a video monitor 32 and may be archived in an image storage device 30. The image processor 28 additionally produces a brightness control signal which is applied to an exposure control circuit 34 to regulate the power supply 16 and thereby the X-ray exposure.

The overall operation of the x-ray apparatus 14 is governed by a system controller 36 that receives commands from the X-ray technician via an operator interface panel 38. Through panel 38, the operator can control the portion of the detector within a field of view by well-known means.

Figure 2:
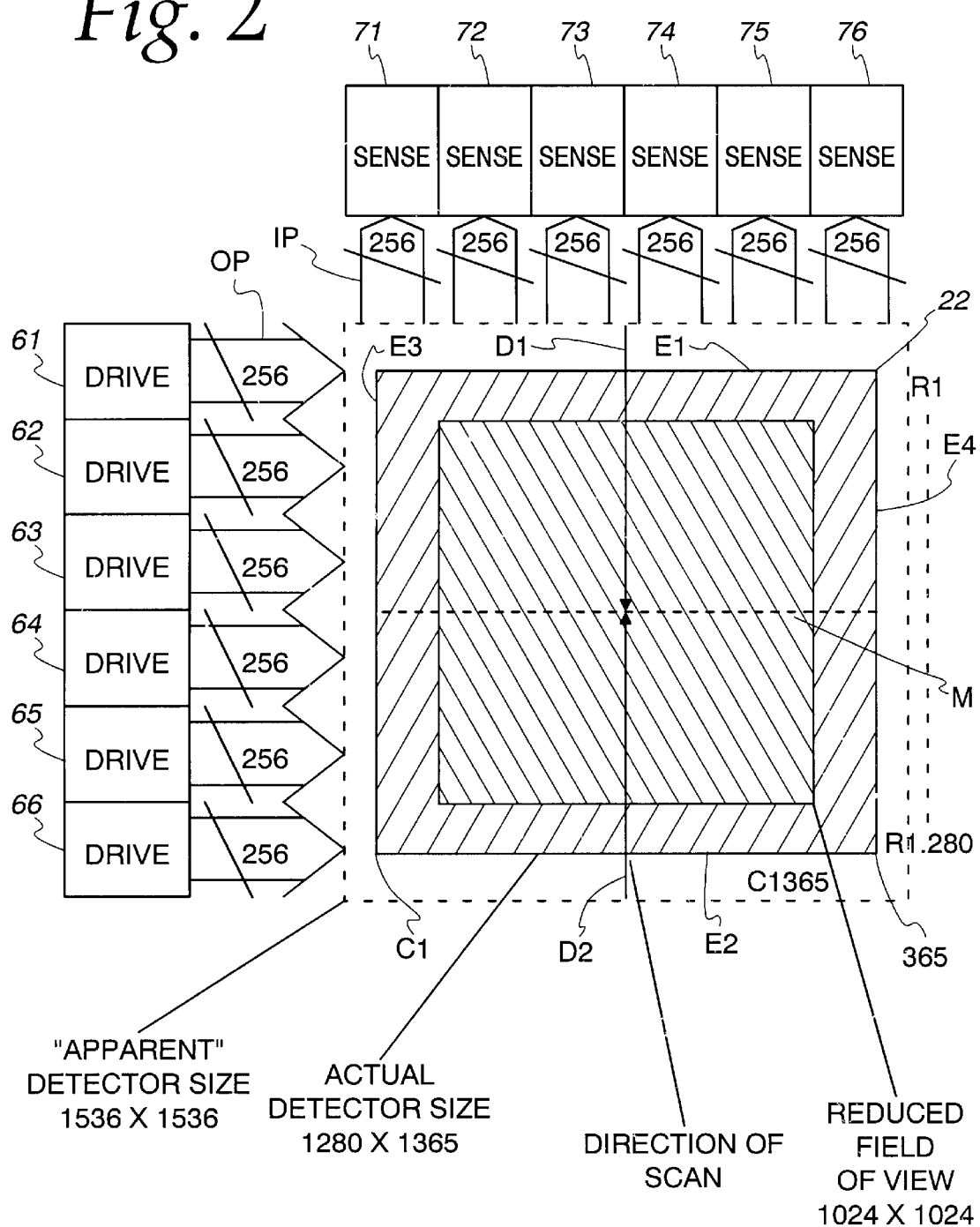
FIG. 2 is a schematic top plan view of the detector shown in FIG. 1, together with exemplary drive and sense circuits.

FIG. 2 depicts detector 22 in order to illustrate the operation of both uncommitted driver outputs as well as scan lines outside a desired field of view. Detector 22 defines edges E1–E4 and a midline M. Detector controller 27 includes drive modules 61–66. Each drive module has 256 outputs OP for a total of 1536 outputs. However, along edge E3, detector 22 has only 1280 elements. As a result, 256 of outputs OP are uncommitted to the detector. 128 of the uncommitted outputs are adjacent edge E1, and 128 of the uncommitted outputs are adjacent edge E2. Due to modularity, six drive modules 61–66, capable of driving a total of 1536 scan lines, are required to operate a detector consisting of 1280 scan lines. Because the detector is split in the middle, and because a drive module can only be operated in one direction, the total number of drive modules required is an even number, with half above and half below midline M. No drive module can straddle the split. Thus, each drive module is coupled exclusively to one part of the split. Each drive module operates like a shift register. Detector 22 includes rows R1–R1280 and columns C1–C1365.

Image processor 28 includes sense circuits 71–76. Each sense circuit has 256 inputs or sense lines IP for a total of 1536 inputs. However, along edge E1, detector 22 has only 1365 elements. As a result, 171 inputs are uncommitted to detector 22. Detector 22 is split across the sense lines in the middle along a midline M. Because of the split in the sense lines, an additional bank of sense electronics (not shown for the sake of simplicity) is located adjacent edge E2 to accomplish readout of the detector. Due to the effects of charge retention, detector 22 is read from the outside in (i.e., in the directions of arrows D1 and D2). Charge retention offsets have higher variation at the beginning of scan (due to the temporal factor in charge retention current decay during what may be a variable expose, or time between frames) and are more predictable at the end. Reading the center (i.e., adjacent line M) last means that charge retention will less likely corrupt the image.

During use, an operator enters a field of view through interface 38. In the example of FIG. 2, the field of view in 1024 by 1024 pixels or elements of detector 22. Thus, there are 256 rows of detector elements with unneeded data outside the field of view. There are 128 rows outside the field of view adjacent edge E1 and 128 rows outside the field of view adjacent edge E2.

Figure 3:
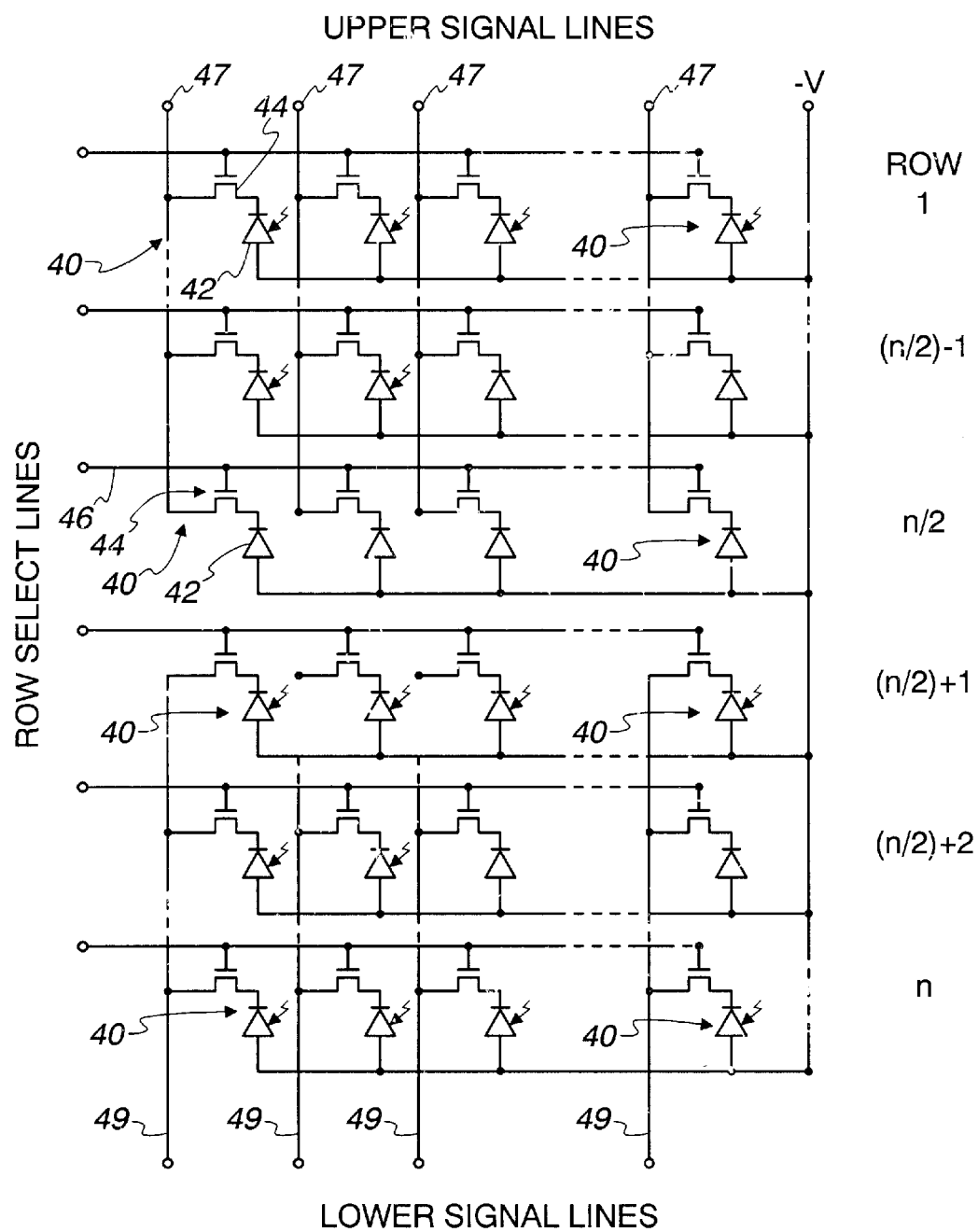
FIG. 3 is a schematic, fragmentary view showing addition details of the detector shown in FIG. 2.

FIG. 3 illustrates the circuitry of the photo detector array 26, which is formed by a matrix of detector elements 40. The detector elements 40 are arranged on an amorphous silicon wafer in a conventional two-dimensional array of m columns and n rows, where m and n are integers. For example, a typical high resolution X ray detector is a square array of 1,000 to 4,000 rows and columns of elements. The example of FIG. 2 has 1280 rows and 1365 columns.

Each detector element 40 includes a photo diode 42 and a thin film transistor 44. The photo diodes 42 are fabricated from a large wafer area ensuring that the photo diode will intercept a sizeable portion of the light produced by the scintillator 24. Each photo diode 42 also has a relatively large capacitance that allows it to store electrical charge which is affected by the photon excitation.

The cathode of the photo diodes 42 in each column of the array is connected by the source-drain conduction path of the associated transistor 44 to a common column signal line (47 or 49) for the column. The anodes of the diodes in each row are connected in common to a source of a negative bias voltage (−v). The gate electrodes of the transistors 44 in each row are connected to a common row select line 46. The row select lines are coupled to the detector controller 27 and the column signal lines are connected to the image processor 28.

As shown in FIG. 3, each column of photo detector elements 40 is divided in half with the upper group of photo elements being connected to upper sense lines 47 and the lower group of detector elements being connected to lower sense lines 49. The upper group includes rows R1–R640 and the lower group includes rows R641–R1280. With this photo detector array structure, when the detector elements are to be read out individually, a row in the upper half and a row in the lower half of the array are read simultaneously. The upper group is read in the direction D1 while the lower group is read in direction D2.

Referring to FIG. 4, the first four lines (i.e., the lines with signals E1, RD1, RS1 and I1) are on a time frame different from the rest of the lines. Shortly after power is applied to the detector, controller 36 takes the initiative to apply the row reset signal RS1, release it, and initialize the drive modules and advance the "1" bit in the shift register of the drive modules as if read out of the detector had begun. In the example of FIG. 2, 128 outputs OP are activated corresponding to the 128 uncommitted outputs adjacent edge E1 of detector 22. After the 128 uncommitted outputs are activated, the first 128 rows of detector 22, R1–R128, are activated by generating pulses A1–A128, which are transmitted to the row select lines shown in FIG. 3. Rows R1–R128 include unneeded data because they lie outside the field of view. Initialize signal I1 indicates that the initialize period begins with the activation of the first uncommitted drive module output adjacent edge E1 and continues through the activation of row R1 through the activation of row R128. When the last row outside the field of view (i.e., row R128) is reached, the detector pauses, waiting for the "read" command RD1 (shown in FIG. 4 as a composite of several more detailed signals) from the system controller 36. When the read command RD1 is received, the detector resumes operating the driver modules as it had before, only the next driver output to be operated will be part of the desired field of view (i.e., row 129 in this example). When readout is complete, controller 36 again applies a row reset signal RS2 for a short while, initializes the drive modules, and again begins to operate the uncommitted drive outputs adjacent edge E1 as if read out had begun, pausing before the first output in the desired field of view until the "read" command RD2 is received from controller 36.

Still referring to FIG. 4, the time period indicated by the "read" signal RD1 illustrates the time period required to scan the part of the detector that contains image data of interest (i.e., rows R129–R1152), regardless of the number of uncommitted driver outputs, or number of scan lines outside the field of view requiring scrubbing. The initialize period, indicated by the initialize signal I1, is the time during which the uncommitted driver module outputs adjacent edge E1 are activated and the time during which the driver module outputs adjacent edge E1 including unneeded data outside the field of view are activated.

Two initialize periods are depicted. Initialize period I1 occurs prior to or during exposure period E1, and initialize period I2 occurs after a "read" period (i.e., RD1) during an exposure period E2. Exposure period E2 is shown as a phantom exposure in order to illustrate how exposure period E2 overlaps with initialize period I2. Period I2 is followed by the beginning of a second phantom read period RD2. If an exposure does not immediately follow the conclusion of a read period RD1, system controller 36 executes the reset and initialize periods as indicated and simply pauses (also shown in phantom), waiting for the next exposure.

The operation for rows R641–R1280 is the same as the above-described operation for rows R1–R640, except that rows R641–R1280 are activated in direction D2 (FIG. 2).

Those skilled in the art will recognize that the preferred embodiments may be altered and modified without departing from the true spirit and scope of the invention as defined in the accompanying claims.

What is claimed is:

1. In an x-ray system for reading data from a detector array comprising a predetermined number of detector elements arranged in rows and columns, said rows comprising a first plurality of rows including unneeded data and a second plurality of rows including data of interest, apparatus for coordinating the activation of the detector elements in relation to the exposure of a patient to x-rays to improve the efficiency with which the data of interest is read comprising:
   an x-ray tube generating x-rays;
   an exposure control arranged to activate the x-ray tube to expose the detector to x-rays during a predetermined first time period;
   a detector controller arranged to activate the first plurality of rows at least partially before or during the first time period and to activate the second plurality of rows after the first time period; and
   an image processor arranged to read the data in said second plurality of rows after the first time period.

2. Apparatus, as claimed in claim 1, wherein the system comprises an operator interface arranged to select a field of view in the detector and wherein the first plurality of rows is outside the selected field of view.

3. Apparatus, as claimed in claim 1, wherein the detector elements define a first edge, a second edge and a midline between the first edge and the second edge, wherein the first plurality of rows comprises a first group adjacent the first edge and a second group adjacent the second edge and wherein the first group is activated in a direction from the first edge to the midline while the second group is activated in a direction from the second edge to the midline.

4. Apparatus, as claimed in claim 1, wherein said rows comprise row select lines, wherein said columns comprise column signal lines, wherein the detector elements each comprise a photodiode and a transistor and wherein the transistor connects the photodiode between a row select line and a column signal line, and wherein detector controller activates each row by switching the transistors in the row to conducting states.

5. Apparatus, as claimed in claim 4, wherein the image processor is coupled to the column signal lines.

6. Apparatus, as claimed in claim 4, wherein the detector elements define a first edge, a second edge and a midline between the first edge and the second edge, and wherein the detector elements are split into a first section in which the column signal lines are located adjacent the first edge and a second section in which the column signal lines are located adjacent the second edge.

7. Apparatus, as claimed in claim 6, wherein the rows of the first section of detector elements are activated from the first edge in a direction toward the midline while the rows of the second section are activated from the second edge in a direction toward the midline.

8. Apparatus, as claimed in claim 7, wherein each photo diode comprises a capacitance allowing charge storage.

9. Apparatus, as claimed in claim 7, wherein the detector controller comprises a plurality of modular drive circuits and wherein each drive circuit is coupled exclusively to the first section or the second section.

10. Apparatus, as claimed in claim 1, wherein the detector controller comprises a plurality of modular drive circuits having a first plurality of outputs unneeded for activation of the detector elements and a second plurality of outputs needed for activation of the detector elements, and wherein the detector controller activates the first plurality of outputs at least partially before or during the first time period and activates the second plurality of outputs after the first time period.

11. In an x-ray system for reading data from a detector array comprising a predetermined number of detector elements arranged in rows and columns, said rows comprising a first plurality of rows including unneeded data and a second plurality of rows including data of interest, a method of coordinating the activation of the detector elements in relation to the exposure of a patient to x-rays to improve the efficiency with which the data of interest is read comprising:
   generating x-rays;
   exposing the detector to x-rays during a predetermined first time period;
   activating the first plurality of rows at least partially before or during the first time period and activating the second plurality of rows after the first time period; and reading the data in said second plurality of rows after the first time period.

12. A method, as claimed in claim 11, and further comprising selecting a field of view in the detector and wherein the first plurality of rows is outside the selected field of view.

13. A method, as claimed in claim 11, wherein the detector elements define a first edge, a second edge and a midline between the first edge and the second edge, wherein the first plurality of rows comprises a first group adjacent the first edge and a second group adjacent the second edge and wherein said activating comprises activating the first plurality of rows in a direction from the first edge to the midline while activating the second group in a direction from the second edge to the midline.

14. A method, as claimed in claim 11, wherein said rows comprise row select lines, wherein said columns comprise column signal lines, wherein the detector elements each comprise a photodiode and a transistor and wherein the transistor connects the photodiode between a row select line and a column signal line, and wherein said activating comprises switching the transistors in the row to conducting states.

15. A method, as claimed in claim 14, wherein said reading comprises coupling the photodiode to the column select lines.

16. A method, as claimed in claim 14, wherein the detector elements define a first edge, a second edge and a midline between the first edge and the second edge, and wherein the detector elements are split into a first section in which the column signal lines are located adjacent the first edge and a second section in which the column signal lines are located adjacent the second edge.

17. A method, as claimed in claim 16, wherein said activating comprises activating the rows of the first section of detector elements from the first edge in a direction toward the midline while activating the rows of the second section from the second edge in a direction toward the midline.

18. A method, as claimed in claim 17, and further comprising storing charge in said photodiodes.

* * * * *